(12) United States Patent
Singer et al.

(10) Patent No.: US 6,576,764 B2
(45) Date of Patent: Jun. 10, 2003

(54) SYNTHESIS AND CRYSTALLIZATION OF PIPERAZINE RING-CONTAINING COMPOUNDS

(75) Inventors: Claude Singer, Kfar Saba (IL); Anita Liberman, Tel Aviv (IL); Nina Finkelstein, Herzliya (IL)

(73) Assignee: Teva Pharmaceutical Industries LTD, Petah Tiqva (IL)

( * ) Notice: Subject to any disclaimer, the term of this patent is extended or adjusted under 35 U.S.C. 154(b) by 0 days.

(21) Appl. No.: 10/283,093

(22) Filed: Oct. 30, 2002

(65) Prior Publication Data

US 2003/0088094 A1 May 8, 2003

Related U.S. Application Data

(62) Division of application No. 09/900,646, filed on Jul. 6, 2001, which is a division of application No. 09/552,485, filed on Apr. 18, 2000.
(60) Provisional application No. 60/130,047, filed on Apr. 19, 1999.

(51) Int. Cl.$^7$ ................................................ C07D 40/04
(52) U.S. Cl. ...................... 544/360; 544/365; 540/555
(58) Field of Search .......................................... 544/360

(56) References Cited

U.S. PATENT DOCUMENTS

| | | | |
|---|---|---|---|
| 4,062,848 A | 12/1977 | van der Burg | 260/268 PC |
| 5,977,099 A | 11/1999 | Nickolson et al. | 514/214 |

FOREIGN PATENT DOCUMENTS

| | | |
|---|---|---|
| DE | 26 14 406 | 10/1976 |

OTHER PUBLICATIONS

Kaspersen, F. M., et al, "The Synthesis of ORG 3770 Labelled with $^3$H, $^{13}$C and $^{14}$C," Journal of Labelled Compounds and Radiopharmaceuticals, vol. XXVII, No. 9, pp. 1055–1068 (1989).

*Primary Examiner*—Mark L. Berch
*Assistant Examiner*—Kahsay Habte
(74) *Attorney, Agent, or Firm*—Kenyon & Kenyon

(57) ABSTRACT

The present invention is directed to methods for the preparation of piperazine ring-containing compounds, particularly mirtazapine. According to the present invention, the mirtazapine intermediate 1-(3-carboxypyridyl-2)-4-methyl-2-phenyl-piperazine is made by hydrolyzing 1-(3-cyanopyridyl-2)-4-methyl-2-phenyl-piperazine with a base where the base is present in a ratio of up to about 12 moles of the base per one mole of 1-(3-cyanopyridyl-2)-4-methyl-2-phenyl-piperazine. The mirtazapine intermediate 1-(3-carboxypyridyl-2)-4-methyl-2-phenyl-piperazine may be made by hydrolyzing 1-(3-cyanopyridyl-2)-4-methyl-2-phenyl-piperazine with potassium hydroxide at a temperature of at least about 130° C. The method of the present invention also includes reacting 2-amino-3-hydroxymethyl pyridine with N-methyl-1-phenyl-2,2'-iminodiethyl chloride to form 1-(3-hydroxymethylpyridyl-2)-4-methyl-2-phenyl piperazine, and adding sulfuric acid to the 1-(3-hydroxymethylpyridyl-2)-phenyl-4-methylpiperazine to form mirtazapine. The present invention also relates to new processes for recrystallization of mirtazapine from crude mirtazapine.

5 Claims, No Drawings

SYNTHESIS AND CRYSTALLIZATION OF PIPERAZINE RING-CONTAINING COMPOUNDS

CROSS-REFERENCE TO RELATED APPLICATION

This is a divisional application of application Ser. No. 09/900,646, filed Jul. 6, 2001, which is a divisional application of application Ser. No. 09/552,485, filed Apr. 18, 2000, which claims the benefit of U.S. Provisional Application No. 60/130,047, filed Apr. 19, 1999 each of which is incorporated herein by reference in its entirety.

FIELD OF THE INVENTION

The present invention relates to synthetic organic chemistry, particularly, to synthesis of piperazine ring-containing compounds, such as mirtazapine, and to the crystallization of mirtazapine from different solvents and solvent systems.

BACKGROUND OF THE INVENTION

Mirtazapine, 1,2,3,4,10,14b-hexahydro-2-methyl-pyrazino[2,1-a]pyrido[2,3-c][2]benzazepine, having the formula I:

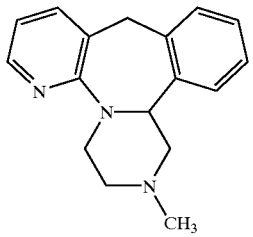

is approved, under the trademark Remeron®, by the U.S. Food and Drug Administration, for the treatment of depression. Mirtazapine has a tetracyclic chemical structure unrelated to other classes of antidepressants such as selective serotonin reuptake inhibitors, tricyclics or monoamine oxidase inhibitors. Mirtazapine belongs to the piperazinoazepine group of compounds.

Mirtazapine may be made by methods described in U.S. Pat. No. 4,062,848. By a process of U.S. Pat. No. 4,062,848 ("the '848 patent"), the mirtazapine intermediate 1-(3-hydroxymethylpyridyl-2-4-methyl-2-phenyl-piperazine is made by a three step process starting with a 2,3-substituted pyridine derivative. Therefore, as shown in Scheme 1, when starting with 2-amino-3-cyano-pyridine, the process of the '848 patent requires four synthetic steps to make mirtazapine. It is desirable to have a process for making mirtazapine that requires fewer steps, and therefore requires less reagent, solvent and time.

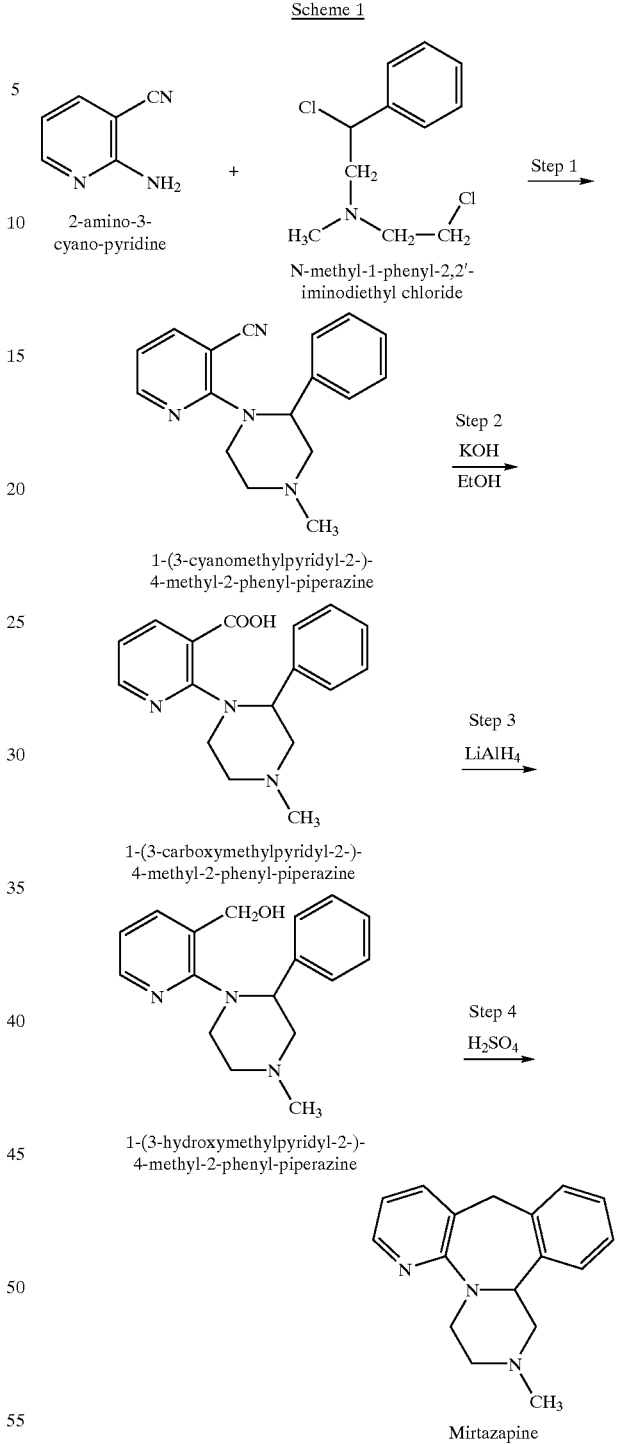

By the process of U.S. Pat. No. 4,062,848 ("the 848 patent"), the mirtazapine intermediate 1-(3-carboxypyridyl-2)-4-methyl-2-phenyl-piperazine is made by the hydrolysis of the nitrile 1-(3-cyanopyridyl-2)-methyl-2-phenyl-piperazine under highly basic conditions of 25 moles of potassium hydroxide (KOH) per mole of nitrile, at high temperature and for long reaction times of 24 hours. These harsh reaction conditions necessitate a great effort in purifying the resulting product as well as creating environmental waste disposal issues associated with neutralizing and disposing of large volumes of concentrated basic solutions. The highly basic conditions and long reaction times make the procedure of the '848 patent very costly, especially in terms of reactor time.

According to the methods of U.S. Pat. No. 4,062,848, crude mirtazapine is recrystallized only in ether and petrol ether 40–60. The solvents ether and petrol ether 40–60 are both very difficult to handle in large scale production.

SUMMARY OF THE INVENTION

The present invention is directed to a method for the preparation of mirtazapine, comprising the steps of: reacting a compound of the formula

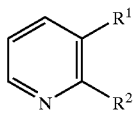

with a compound of the formula

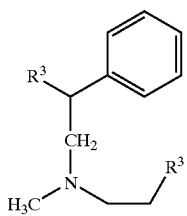

to form a compound of the formula

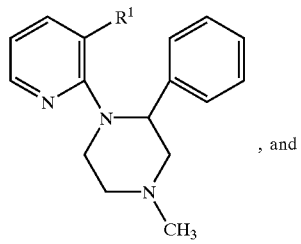

, and adding a ring closing reagent to the compound of the formula

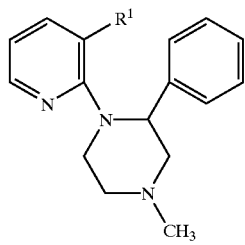

to form mirtazapine, wherein $R^1$ is selected from the group consisting of hydroxymethyl, chloromethyl, bromomethyl and iodomethyl; $R^2$ is amine; and $R^3$ is selected from the group consisting of chloro, fluoro, bromo and iodo.

In a preferred embodiment of the present invention is directed to a method for the preparation of mirtazapine, comprising the steps of reacting 2-amino-3-hydroxymethyl pyridine with N-methyl-1-phenyl-2,2'-iminodiethyl chloride to form 1-(3-hydroxymethylpyridyl-2)-4-methyl-2-phenyl piperazine, and adding sulfric acid to the 1-(3-hydroxymethylpyridyl-2)-4-methyl-2-phenyl-piperazine to form mirtazapine.

Further, it has now been discovered that the mirtazapine intermediate 1-(3-carboxypyridyl-2)-4-methyl-2-phenyl-piperazine may be made by hydrolysis of the nitrile 1-(3-cyanopyridyl-2)-4-methyl-2-phenyl-piperazine using new more favorable reaction conditions. The new reaction conditions of the present invention include a low mole to mole ratio of potassium hydroxide to nitrile and shorter reaction times.

The present invention relates to a improved process for making 1-(3-carboxypyridyl-2)-4-methyl-2-phenyl-piperazine by hydrolyzing 1-(3-cyanopyridyl-2)-4-methyl-2-phenyl-piperazine comprising the step of reacting 1-(3-cyanopyridyl-2)-4-methyl-2-phenyl-piperazine with a base wherein the base is present in a ratio of up to about 12 moles of the base per one mole of 1-(3-cyanopyridyl-2)-4-methyl-2-phenyl-piperazine.

In a preferred embodiment of the present invention, the ratio of the base to 1-(3-cyanopyridyl-2)-4-methyl-2-phenyl-piperazine is about 12 moles of base to about one mole of 1-(3cyanopyridyl-2)-4-methyl-2-phenyl-piperazine to about 9 moles of base to about one mole of 1-(3-cyanopyridyl-2)-4-methyl-2-phenyl-piperazine.

In another preferred embodiment of the present invention, the base is potassium hydroxide or sodium hydroxide.

In another embodiment of the present invention, the mixture of the 1-(3-cyanopyridyl-2)-4-methyl-2-phenyl-piperazine and the base is heated to at least about 130° C.

In another embodiment of the present invention, the hydrolysis of 1-(3-cyanopyridyl-2)-4-methyl-2-phenyl-piperazine is carried out in a mixture water and a solvent selected from the group consisting of methanol, ethanol, propanol, isopropanol, butanol, dimethylformamide, dimethylacetamide and dimethylsulfoxide.

The present invention also relates to improved processes for making mirtazapine from crude mirtazapine comprising the steps of (a) heating a mixture of crude mirtazapine and solvent; and (b) isolating mirtazapine.

In a preferred embodiment of the present invention, water is added to the heated mixture of mirtazapine and solvent to facilitate precipitation of mirtazapine.

In an additional embodiment of the present invention, preferred solvents are methanol, ethanol, isopropanol, acetone, toluene, and hexane and mixtures thereof.

In an additional embodiment of the present invention, preferred solvents are toluene, hexane, and methylene chloride.

DETAILED DESCRIPTION OF THE INVENTION

The present invention relates to a novel process for preparing piperazine ring-containing compounds, such as mirtazapine, as described in Scheme 2 below. The process of the present invention is advantageous over prior art processes due to, inter alia, the higher yield, smaller number of steps in relation to the alternative methods, and minimized raw material costs.

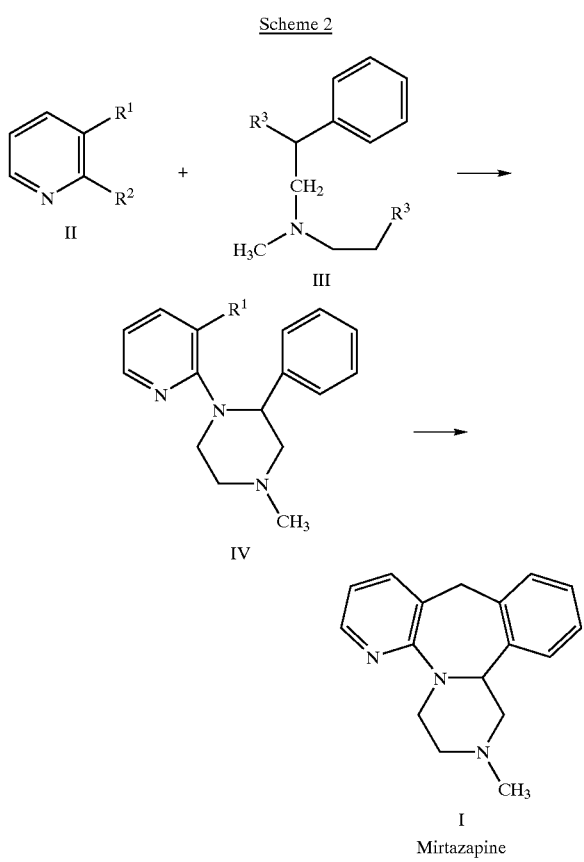

Scheme 2

IV

I
Mirtazapine

More particularly, the present invention relates to the process of making mirtazapine from compounds of the formulae II, III and IV. In the process of the present invention the compound of formula II in Scheme 2 above, wherein $R^1$ denotes hydroxymethyl, chloromethyl, bromomethyl or iodomethyl, and $R^2$ denotes amine, preferably —$NH_2$, is reacted with the compound of formula III in Scheme 2 above, wherein $R^3$ denotes chloro, fluoro, bromo or iodo, to form the compound of formula IV wherein $R^1$ is defined as above.

In the process of the present invention, the compound of formula II is dissolved in a solvent such as methylene chloride. The compound of formula III is added to the solvent mixture and the resulting mixture is heated. Preferably the reaction mixture is heated to the reflux temperature of the solvent. The mixture is heated to form the compound of formula IV. Mirtazapine is then prepared by ring closure of the compound of formula IV. Ring closure of the compound of formula IV may be performed using a ring-closing reagent. Suitable ring closing reagents are dehydrating or dehydrohalogenating agents. Dehydrating or dehydrohalogenating agents that may be added to the reaction mixture for this purpose include acids, such as sulfuric acid, concentrated sulfuric acid, concentrated hydrochloric acid, trifluoroacetic acid, phosphoric acid, polyphosphoric acid (PPA), phosphorus oxychloride, phosphorus trioxide, phosphorus pentoxide and Lewis acids, such as aluminum chloride, ferric chloride, zinc chloride, tin chloride, titanium chloride, boron trifluoride, antimony pentachloride and zirconium tetrachloride.

Dehydrating agents that are particularly preferred are sulfuric acid and phosphorus derivatives, such as PPA and phosphorus oxychloride. Concentrated sulfuric acid most preferred. A particularly preferred dehydrohalogenating agent is aluminum chloride.

In a preferred embodiment of the present invention the compounds of the formulae II, III and IV are compounds of the formulae II', III' and IV' respectively as shown in Scheme 3 below. In an embodiment of the present invention, 2-amino-3-hydroxymethyl pyridine is reacted with N-methyl-1-phenyl-2,2'-iminodiethyl chloride to form 1-(3-hydroxymethylpyridyl-2)-4-methyl-2-phenyl-piperazine. In the present invention, 2-amino-3-hydroxymethyl pyridine (II') is added to a solvent. Suitable solvents include 1,2-dichloroethane, methylene chloride, dimethylformamide, dimethylacetamide and dimethylsulfoxide. N-Methyl-1-phenyl-2,2'-imidodiethyl-chloride (III') is added to the solvent mixture and the resulting mixture is heated. Preferably the reaction mixture is heated to the reflux temperature of the solvent. The mixture is heated until 1-(3-hydroxymethylpyridyl-2)-4-methyl-2-phenyl-piperazine is formed and the reaction is complete. A suitable time is about six to about 24 hours. The 1-(3-hydroxymethylpyridyl-2)-4-methyl-2-phenyl-piperazine is then converted to mirtazapine by ring closure.

The ring closure of 1-(3-hydroxymethylpyridyl-2)-4-methyl-2-phenyl-piperazine is performed under strongly dehydrating ($R^1$=OH) conditions, preferably at an elevated temperature. Suitable dehydrating agents, include acids, such as sulfuric acid, concentrated hydrochloric acid, trifluoroacetic acid, phosphoric acid, polyphosphoric acid (PPA), phosphorus oxychloride, phosphorus trioxide and phosphorus pentoxide. Dehydrating agents that are particularly preferred are sulfuric acid and phosphorus derivatives, such as PPA and phosphorus oxychloride. Concentrated sulfric acid is most preferred.

Scheme 3

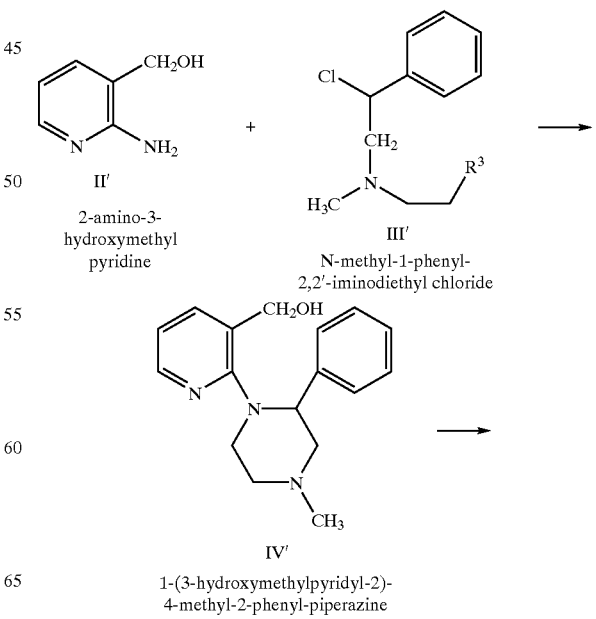

II'
2-amino-3-hydroxymethyl pyridine

III'
N-methyl-1-phenyl-2,2'-iminodiethyl chloride

IV'
1-(3-hydroxymethylpyridyl-2)-4-methyl-2-phenyl-piperazine

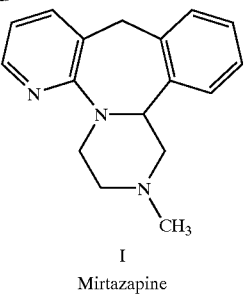

I
Mirtazapine

The present invention also provides new processes for making the mirtazapine intermediate 1-(3-carboxypyridyl-2)-4-methyl-2-phenyl-piperazine from the nitrile 1-(3-cyanopyridyl-2)-4-methyl-2-phenyl-piperazine where the nitrile is (I) hydrolyzed by base using a new low mole to mole ratio of base to the nitrile 1-(3-cyanopyridyl-2)-4-methyl-2-phenyl-piperazine and (ii) hydrolyzed using short reaction times.

Where the present invention provides improved methods for making the mirtazapine intermediate 1-(3-carboxypyridyl-2)-4-methyl-2-phenyl-piperazine, the nitrile 1-(3-cyanopyridyl-2)-4-methyl-2-phenyl-piperazine is dissolved in a mixture of water and organic solvent. Preferred organic solvents include polar aprotic solvents and alcohols. Polar aprotic organic solvents such as dimethylformamide, dimethylacetamide and dimethylsulfoxide and the like are preferred. Preferred alcohols are methanol, ethanol, propanol, isopropanol, butanol and the like. A suitable amount of base, such as potassium hydroxide or sodium hydroxide, is added to the reaction mixture. An amount of base, such as potassium hydroxide or sodium hydroxide, of up to about 12 moles of base per mole of nitrile (for example 12:1 KOH:nitrile) is preferred. Amounts of base, such as potassium hydroxide, in the ratio of about 9 moles of potassium hydroxide per one mole of nitrile (9:1 KOH:nitrile), to about 12 moles of potassium hydroxide per mole of nitrile (12:1 KOH:nitrile) are preferred.

In the present invention, the mixture of the nitrile 1-(3-cyanopyridyl-2)-4-methyl-2-phenyl-piperazine, solvent and base is heated to at least about 130° C. Reaction temperatures of about 130° C. to about 150° are preferred. In an embodiment of the present invention, the reaction may be conducted under pressure to facilitate the attainment of high temperatures. A pressure of at least about 3 atmospheres is preferred. Pressures of at least about 3 atmospheres to about 4 atmospheres are more preferred. The reaction mixture is heated until the reaction is complete. The completion of the reaction may be monitored by HPLC. The amount of time needed for the completion of the hydrolysis of the nitrile varies with the temperature of the reaction. Higher reaction temperatures generally require shorter reaction times, while lower reaction temperatures generally requires longer reaction times. While not limiting the reaction time of the present invention, preferred reaction times of the present invention may be from about 2 hours to about 8 hours. Upon completion of the reaction, the pH of the reaction mixture is lowered, preferably to a pH of about 6 to about 7. Preferably the pH is lowered with hydrochloric acid. The mirtazapine intermediate, 1-(3-cyanopyridyl-2)-4-methyl-2-phenyl-piperazine is isolated following washing and filtration of the reaction mixture.

In an additional embodiment of the present invention, the reaction mixture of the nitrile 1-(3-cyanopyridyl-2)-4-methyl-2-phenyl-piperazine, and potassium hydroxide, is heated while using a minimum amount of water, such as about 0.25–1 mL of water per gram of KOH, and small amounts of an aprotic solvent such as dimethylformamide, dimethylacetamide and dimethylsulfoxide, such as about 0.1 to 0.5 grams of aprotic solvent per gram of nitrile, under very concentrated conditions or almost neat conditions at atmospheric pressure. The mirtazapine intermediate, 1-(3-cyanopyridyl-2)-4-methyl-2-phenyl-piperazine is isolated following washing and filtration of the reaction mixture.

The new processes of the present invention for making the mirtazapine intermediate 1-(3-carboxypyridyl-2)-4-methyl-2-phenyl-piperazine from the nitrile 1-(3-cyanopyridyl-2)-4-methyl-2-phenyl-piperazine significantly reduce the quantity of potassium hydroxide used, from 25 moles of potassium hydroxide per mole of the nitrile as in the '848 patent, to about 12 moles or less of potassium hydroxide to one mole of the nitrile. The reduction in the amount of base needed considerably simplifies the work-up of the reaction and minimizes environmental problems.

The present invention also provides new methods for making pure mirtazapine by purifying crude mirtazapine by recrystallization. Upon the ring closure of 1-(3-hydroxymethylpyridyl-2)-4-methyl-2-phenyl-piperazine to form mirtazapine, the crude product, mirtazapine, is purified by recrystallization.

It has been discovered that common solvents such as toluene or methylene chloride and solvent systems such as alcohol-water can be used in the recrystallization of crude mirtazapine. According to the present invention, crude mirtazapine is suspended in a suitable solvent. Preferred solvents include methanol, ethanol, isopropanol, and acetone and mixtures thereof, or mixtures of one or more of those solvents with water. Additional preferred solvents also include toluene, hexane, and methylene chloride. Solvent mixtures of water and ethanol are more preferred. Solvent mixtures of ratios of about 1:1 to about 1:4 ethanol:water are preferred.

In the present invention, the suspension of crude mirtazapine and solvent is heated to a suitable temperature. Suitable temperatures include, for example, the reflux temperature of the solvent system being used in any particular embodiment of the present invention. For example, in an embodiment of the present invention where toluene is the solvent, a temperature of about 110° C. is suitable. Purified mirtazapine precipitates upon cooling of the reaction mixture. Filtration and drying of the resulting precipitate yields purified, recrystallized mirtazapine.

In a further example, crude mirtazapine is suspended in a solvent such as ethanol, and the mixture is heated to reflux. Water is then added dropwise and the solution is cooled to facilitate precipitation of mirtazapine. The precipitate is purified by filtration, washing and drying to yield purified mirtazapine. The crystallized mirtazapine may be a water adduct thereby containing up to 3% water by weight (3% w/w).

The solvents and solvent systems of the present invention are suitable for large sale reactions, and are more suitable for large scale reactions than ether or petrol ether 40–60. Additionally, the crystallization yield can be substantially improved when using the solvent system of the present invention.

Mirtazapine and mirtazapine intermediates, 1-(3cyanopyridyl-2)-4-methyl-2-phenyl-piperazine and 1-(3-carboxypyridyl-2)-4-methyl-2-phenyl-piperazine each contain an asymmetric carbon atom, as a result of which separate optical isomers may be prepared in addition to a racemic mixtures. Processes of the present invention include these optical isomers just as the racemic mixtures are included in the invention.

In accordance with the present invention, mirtazapine produced by the process of the present invention may be prepared as pharmaceutical compositions that are particularly useful for the treatment of depression. Such compositions comprise a therapeutically effective amount of mirtazapine with pharmaceutically acceptable carriers and/or excipients known to one of skill in the art.

EXAMPLES

The following examples are given for the purpose of illustrating the present invention and shall not be construed as being limitations on the scope or spirit of the invention.

Example 1

Preparation of 1-(3Hydroxymethylpyridyl-2-)-4-Methyl-2-Phenyl-Piperazine

In a 50 mL three-necked flask equipped with a mechanical stirrer, a condenser and a thermometer 1 g (0.008 mole) of 2-amino-3-hydroxymethyl pyridine and 20 mL of 1,2-dichloroethane were charged. The mixing is started and to the suspension 2.8 g (0.012 mole) of N-methyl-1-phenyl-2,2'-iminodiethyl-chloride are added. The reaction mixture is heated to reflux (~80° C.) and maintained at this temperature for six hours.

After six hours the reaction mixture is cooled and the solvent (1,2-dichloroethane) is removed by dry distillation. A yellowish powder is obtained which contains 1.8 g 1-(3-hydroxymethyl pyridyl-2)-4-methyl-2-phenyl-piperazine (yield 80%). This powder can be used without additional purification for the preparation of mirtazapine.

Example 2

Preparation of Mirtazapine

In a 50 mL three-necked flask equipped with a mechanical stirrer, a condenser and a thermometer 1.8 g of 1-(3-hydroxymethyl pyridyl-2)-4-methyl-2-phenyl-piperazine are added to ~5 mL of concentrated sulfuric acid that was previously cooled to 10° C. The obtained solution is mixed at room temperature for 4 hours, then heated for one hour to about 50° to 600° C. After cooling, the reaction mass is added to 25 g of ice under mixing and neutralized with a concentrated ammonia solution or sodium hydroxide. The formed precipitate is separated by filtration. The mother liquor is evaporated to dryness under vacuum. Both the formed precipitate and the residue from the mother liquor are each suspended in~20 mL of isopropanol. The combined isopropanol extracts are evaporated to dryness. An oil is obtained which contains 1.35 g of mirtazapine (yield 80%).

Example 3

Preparation of Mirtazapine 1-(3-Hydroxymethylpyridyl-2)-4-methyl-2-phenyl-piperazine (1.8 g) is added to ~5 mL of concentrated sulfuric acid. The resulting solution is mixed at 350° C. for 6 hours. After cooling, the reaction mixture is added to 25 g of ice under mixing and basified with a concentrated ammonia solution or sodium hydroxide solution to pH=10. The separated precipitate is extracted into methylene chloride and the extract is evaporated to dryness; 1.6 g of Mirtazapine is obtained (yield 95%).

Example 4

Preparation of 1-(3-Carboxypyridyl-2-)-4-Methyl-2-Phenyl-Piperazine 1-(3-cyanopyridyl-2-)-4-methyl-2-phenyl-piperazine (54 g) is dissolved in 340 mL of ethanol and 34 mL of water. Potassium hydroxide flakes, 85% (113 g), are added and the reaction mixture is heated in an autoclave to 140° C. The pressure increases to 3–4 atmospheres and the reaction mixture is maintained under pressure with mixing for 5 hours. After 5 hours, the reaction mixture is cooled, the ethanol is removed from the mixture by vacuum distillation, fresh water and toluene are added and the 2 phases are separated. The water solution is neutralized with hydrochloric acid (HCl) to pH=6.5–7. At pH=6.5–7 the water is evaporated and toluene is added. The inorganic salts are filtered and the toll one solution is evaporated to dryness yielding 52 g of 1-(3-carboxypyridyl-2-)-4-methyl-2-phenyl-piperazine (yield: 90%).

Example 5

Preparation of 1-(3-Carboxypyridyl-2-)-4-Methyl-2-Phenyl-Piperazine

Potassium hydroxide (150 g of KOH flakes, 85%) and 75 mL of water and 6.5 g of DMSO are added to 1-(3-cyanopyridyl-2-)-4-methyl-2-phenyl-piperazine (54 g) and the reaction mixture is heated to 145–150° C. and mixed for 8 hours. After 8 hours, the inorganic phase containing water and potassium hydroxide (KOH) is separated and the organic phase, containing mainly a product oil, is cooled. Fresh water and toluene are added and the two phases are separated. The aqueous solution is neutralized with HCl to pH=6.5–7. At pH=6.5–7, the water is evaporated and toluene is added. The inorganic salts are filtered and the toluene solution is evaporated to dryness yielding 52 g of 1-(3-carboxypyridyl-2-)-4-methyl-2-phenyl-piperazine (yield: 90%).

Example 6

Recrystallization of Mirtazapine

Mirtazapine (20 g), obtained as in Examples 2 and 3, is suspended in 20 mL of ethanol and heated to reflux. At reflux, 40 mL of water is added dropwise to the solution over one hour followed by cooling to 100° C. The resulting filter cake is washed with a solution of water:ethanol (2:1) and dried at 60° C. under a vacuum. Crystallized mirtazapine, 18 g, is obtained in 90% yield.

Table 1 sets forth a summary of additional experiments generally following procedures described above wherein the Yield % is the percent yield of mirtazapine crystals from crude mirtazapine and the Purity % is the percent purity as compared to a mirtazapine standard.

TABLE I

Purification of Crude Mirtazapine by Recrystallization

| Solvent system | Ratio of solvents ml:ml/g | Conditions | Yield[1] % |
|---|---|---|---|
| hexane | 10 | reflux | 55 |
| toluene | 3 | reflux | 32 |
| toluene | 2 | reflux | 53 |
| acetone/water | 6:25 | 25° C. | 65 |
| ethanol/water | 7:10 | reflux | 67 |
| methanol/water | 2.25:1.5 | reflux | 67 |
| ethanol/water | 1.5:2 | reflux | 72 |
| isopropyl/water | 1.65:2 | reflux | 60 |
| acetone-water | 3:2 | reflux | 53 |
| ethanol/water | 1:1.3 | reflux | 70 |
| ethanol/water | 1.3:1.75 | reflux | 90.3 |
| ethanol/water | 1:4 | reflux | 100 |
| ethanol/water | 1.1:1.2 | reflux | 87.8 |
| ethanol/water | 0.8:0.9 | reflux | 90 |
| ethanol/water | 0.8:1 | reflux | 57 |
| ethanol/water | 0.6:0.7 | reflux | 89.1 |
| ethanol/water | 0.35:0.7 | reflux | 91.5 |
| ethanol/water | 0.6:0.69 | reflux | 87 |
| ethanol/water | 2:2.8 | reflux | 95.6 |

[1]g mirtazapine crystals 100%/g mirtazapine crude 100%

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rule of law.

We claim:

1. A method for the preparation of a mirtazapine intermediate comprising reacting a compound of the formula

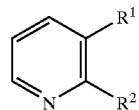

with a compound of the formula

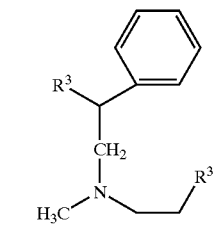

to form a compound of the formula

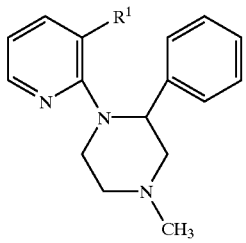

wherein $R^1$ is selected from the group consisting of hydroxymethyl, chloromethyl, bromomethyl and iodomethyl; $R^2$ is amino; and $R^3$ is selected from the group consisting of chloro, fluoro, bromo and iodo.

2. The method of claim 1, wherein $R^1$ is hydroxymethyl.

3. The method of claim 2, wherein $R^2$ is —$NH_2$, and $R^3$ is chloro.

4. The method of claim 1, wherein the reacting step is performed at reflux in a solvent selected from the group consisting of 1,2-dichloroethane, methylene chloride, dimethylformamide, dimethylacetamide and dimethylsulfoxide.

5. The method of claim 4, wherein the solvent is methylene chloride.

* * * * *